United States Patent [19]

Lam et al.

[11] Patent Number: 5,610,044
[45] Date of Patent: Mar. 11, 1997

[54] MICROORGANISMS WITH MANNOPINE CATABOLIZING ABILITY

[76] Inventors: Stephen T. Lam, 8900 Jeanew Ct., Raleigh, N.C. 27613; Nancy R. Torkewitz, 7301 Gates Rd., Hurdle Mills, N.C. 27541; Chandra S. Nautiyal, 2800, rue de l'anse, Sainte-Foy, Canada, G1 W 2G5; Patrice Dion, 2774, rue de Montarville, Sainte-Foy, Canada, G1 W 1V3

[21] Appl. No.: 346,331

[22] Filed: Nov. 29, 1994

Related U.S. Application Data

[63] Continuation of Ser. No. 102,394, Aug. 5, 1993, abandoned, which is a continuation of Ser. No. 590,905, Oct. 1, 1990, abandoned.

[51] Int. Cl.⁶ ............................. C12N 1/20; C12N 1/21; C12N 15/09; C12N 15/56
[52] U.S. Cl. ................................. 435/172.3; 435/252.3; 435/320.1; 435/252.34; 536/23.2
[58] Field of Search ............................. 435/69.1, 172.3, 435/320.1, 252.3, 252.34, 253.3; 536/23.1, 23.2

[56] References Cited

FOREIGN PATENT DOCUMENTS 0203863 12/1986 European Pat. Off. .

OTHER PUBLICATIONS

Nautiyal et al, J. Bacteriol., 173(9):pp.2833–2841 (May 1991).

Tepfer, Ri T–DNA from *Agrobacterium rhizogenes*: "A Source of Genes Having Applications in Rhizophere Biology and Plant Development, Ecology and Evolution" in Plant–Microbe Interactions, vol. 3 (Editors Kosuge and Nester), McGraw–Hill Publishing Co. (1989) pp. 294–343.

Tepfer et al., *J. Bacteriol.*, 170:1155–1161 (1988).

Tepfer et al. *Molecular Genetics of Plant–Microbe Interactions*, Palieros and Verma, Editors, RPS Press, (19 pp. 139–144).

Weller in *Annual Rev. Phytopathol.*, 26:379–407 (1988).

Beaulieu et al., Can. J. Microbiol., 34:843–849 (1988).

Nautiyal et al., Appl. & Enviroment. Microbiol., 56(8)2576–2579 (1990).

Tremblay et al., Appl. & Enviroment. Microbiol., 53(7)1519–1524 (1987).

Dessaux et al., Molec. Gen. Genet., 208:301–308 (1987).

*Primary Examiner*—John L. Leguyader
*Assistant Examiner*—Philip W. Carter
*Attorney, Agent, or Firm*—Gary M. Pace; Andrea C. Walsh

[57] ABSTRACT

The present invention relates to a method for enhancing colonization of desired microorganisms in a localized environment comprising introducing into said localized environment a genetically engineered microorganism comprising a gene comprising a DNA sequence coding for one or more substrate utilizing protein, wherein said substrate utilizing protein confers a competitive effective ability to utilize a substrate by a microorganism in which it is genetically engineered, as well as the isolated genes and the genetically engineered microorganisms of such a method.

7 Claims, 1 Drawing Sheet

1

MICROORGANISMS WITH MANNOPINE CATABOLIZING ABILITY

This application is a continuation of application Ser. No. 08/102,394, filed Aug. 5, 1993, now abandoned, which is a continuation of application Ser. No. 07/590,905 filed Oct. 1, 1990, now abandoned.

BACKGROUND

This invention relates to microorganisms that have been improved by genetically engineering an ability to utilize a given substrate, thereby possessing a competitive advantage in their ability to colonize a given localized environment such as a rhizosphere.

The beneficial effects of bacteria that naturally colonize the environment near plant roots (the rhizosphere) has been known for some time. See, for example, Weller, in: *Ann. Rev. Phyopathol.* 26:379–407 (1988), which provides a comprehensive review. One way to encourage preferential colonization of a desired species of microorganism is to introduce a microorganism that has an ability to produce a antimicrobial substance such as is described in copending U.S. patent application Ser. No. 579,457, filed Sep. 7, 1990. Another way to encourage preferential colonization of a desired species of microorganism would be to engineer the desired species to confer a superior ability to utilize a limited substrate occurring in the localized environment in which it occurs. In this way, the colonization of the desired species is enhanced and colonization of undesired inferior substrate utilizing species is controlled.

Chemicals found in the rhizosphere called calystegins have been described as being used by certain microorganisms as a sole carbon source, with the ability to utilize the calystegins being attributable to a segment of DNA [Tepfer et al., *Molecular Genetics of Plant/Microbe Interactions*, Palacios and Verma, editors, APS Press, (1988) PP. 139–144; Tepfer et al., *J. Bacteriol.*, 170:1153–1161 (1988); Tepfer et al., "Ri T-DNA from Agrobacterium rhizogenes: a source of genes having applications in rhizophere biology and plant development, ecology and evolution" in Plant-Microbe Interactions, vol. 3 (editors Kosuge and Nester), McGraw-Hill Publishing Co., (1989) pp 294–343; Tepfer et al., European Patent Application 203863, published Dec. 3, 1986].

SUMMARY OF THE INVENTION

One aspect of the present invention is a gene comprising a DNA sequence coding for one or more substrate utilizing protein, wherein said substrate utilizing protein confers a competitive effective ability to utilize a substrate by a microorganism in which it is genetically engineered.

Another aspect of the present invention is a genetically engineered microorganism comprising a gene according to the present invention, which gene has been genetically engineered into the microorganism and confers a competitive effective ability to utilize a substrate.

Another aspect of the present invention is a method for enhancing colonization of desired microorganisms in a localized environment comprising introducing into said localized environment a genetically engineered microorganism according to the present invention.

Another aspect of the present invention is a method for controlling the presence of an undesired microorganism in a localized environment comprising enhancing colonization of a desired microorganism in the same localized environment according to the colonization enhancement method of the present invention.

DETAILED DESCRIPTION OF THE INVENTION

Figure 1:
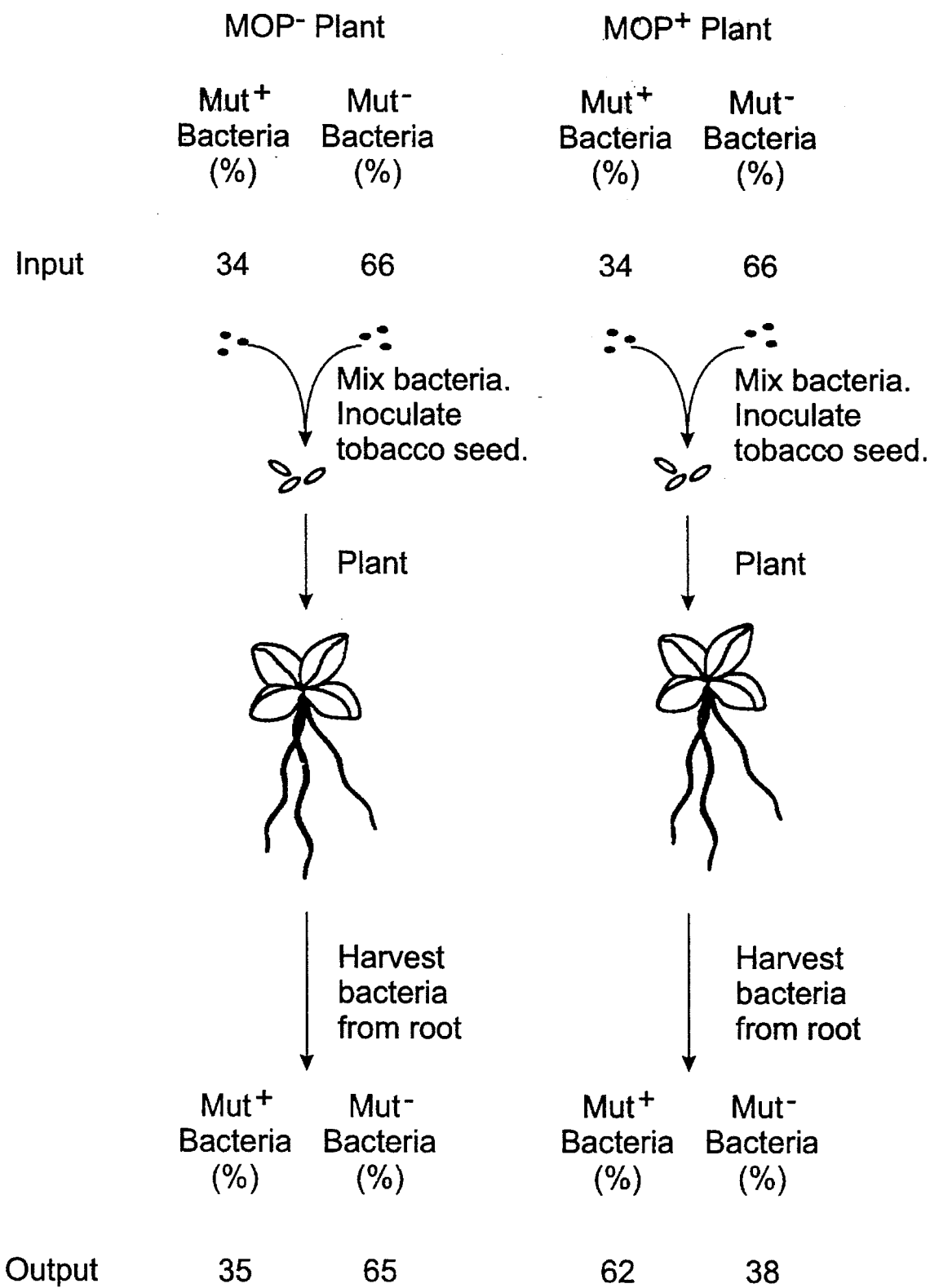
FIG. 1: Competition between a mannopine-utilizing bacterium and its non-utilizing mutant. The competition assay is performed as described in Example 4.

To assist in interpreting the meaning and scope of the present invention, the following terms are intended to have the meanings as described below, unless otherwise indicated. All references cited in this application are herein incorporated by reference for their relevant teachings.

Antimicrobial Effective Amount: An amount of a substance or organism, e.g., substrate utilizing microorganism, sufficient to cause significant inhibition of growth and division of certain microbial species or significant death or significant reduction of population of certain microbial species. Significant inhibition of growth and division of certain microbial species or significant reduction of number of population of certain microbial species means inhibition of growth or division large enough to result in a net decrease in the number of members in the population of the certain species and eventually threaten the survival of the certain species in the localized environment and/or lead to eventual extinction of the species in the localized environment. Preferably, the certain microbial species is a nonsubstrate utilizing species. Preferably, the net loss will be on the order of 50 percent and more preferably the loss will be about an order of magnitude to about 10 percent of the population in the absence of a substrate utilizing species.

Bacterial Strain: A race or subculture of a bacterial species exhibiting certain distinct phenotypic characteristics which enable it to be distinguished from other members of the same species.

Coding DNA Sequence: A DNA sequence which, when transcribed and translated, results in the formation of a cellular polypeptide.

Competitive Effective Ability: The ability of a substrate utilizing organism to more efficiently utilize a given substrate as an energy or carbon source such that its rate of growth is significantly greater than the rate of growth of a nonutilizing organism. A greater growth rate means enhancement of growth and division of certain microbial species, e.g., significant increases in the population of certain substrate utilizing microbial species. Significant increases in the population of certain microbial species means a net increase in the number of members in the population of substrate utilizing species when compared to the number of members in the population of the nonutilizing microbial species. Preferably, the rate of growth of the utilizing organism is at least two times greater than the nonutilizing organism, more preferably the rate of growth is at least ten times greater than the nonutilizing organism, most preferably the rate of growth is at least 100 times greater than the nonutilizing organism.

Derived from: In the context of this application genes, parts of genes, or other DNA sequences "derived from" other DNA sources embraces genes, parts of genes or other DNA sequences, identical to or substantially homologous to the DNA source material.

Gene: A discrete chromosomal region comprising regulatory DNA sequences responsible for the control of expression, i.e., transcription and translation, and of a coding sequence which is transcribed and translated to give one or more distinct polypeptide.

Genetically Engineered Microorganism: A single celled microorganism that has introduced into it genetic material consisting of a DNA sequence, which DNA sequence does not naturally occur in the microorganism or which does not naturally occur at the position or frequency found in the genetically engineered microorganism. Not naturally occurring preferably means that the introduced DNA sequence has been obtained from a species different form the species into which it is introduced or that the DNA sequence is a significant mutation from the naturally occurring DNA sequence. A significant mutation in a DNA sequence is preferably a mutation that produces a DNA sequence or a protein that is not substantially homologous to the naturally occurring DNA sequence or protein coded thereby.

Hybrid Sequence or Hybrid Gene: A DNA sequence containing at least two heterologous parts, e.g., parts derived from, or having substantial sequence homology to, pre-existing DNA sequences which are not associated in their pre-existing states. The pre-existing DNA sequences may be of natural or synthetic origin.

Localized Environment: An environment that is spatially uninterrupted and that exhibits similar characteristics for microbial growth, e.g., exhibiting similar characteristics of nutrients, light, pressure, moisture, temperature, atmospheric content, chemical composition, etc. Such localized environments include the environment near the roots of plants both in the soil and submersed in water (hydroponic root environment).

Phenotypic Trait: An observable property resulting from the expression of one or more genes.

Plant cell: The structural and physiological unit of plants, consisting of a protoplast and the cell wall. The term "plant cell" refers to any cell which is either part of or derived from a plant. Some examples of cells encompassed by the present invention include differentiated cells that are part of a living plant; differentiated cells in culture; undifferentiated cells in culture; the cells of undifferentiated tissue such as callus or tumors; seeds; embryos; propagules and pollen.

Plant Tissue: A group of plant cells organized into a structural and functional unit. Any tissue of a plant in plants or in culture. This term includes, but is not limited to, whole plants, plant cells, plant organs, plant seeds, protoplasts, cell culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

Pre-existing DNA Sequence: A DNA sequence that exists prior to its use, in toto or in part, in a product or method according to the present invention. While such pre-existence typically reflects a natural origin, pre-existing sequences may be of synthetic or other origin.

Rhizosphere: An environment near the roots of plants both in the soil and submersed in water (hydroponic root environment). Near the roots means within a distance of the roots close enough that chemicals produced preferentially in the root cells are detectable.

Substantial Sequence Homology: Substantial functional and/or structural equivalence between sequences of nucleotides or amino acids. Functional and/or structural differences between sequences having substantial sequence homology will be de minimus. The sequences that differ from the natural sequences are usually variants of the natural sequence. A variant of a natural sequence is a modified form of the natural sequence that performs the same function. The variant may be a mutation, or may be a synthetic sequence. A de minimus functional difference results from a nucleotide or amino acid sequence that codes for a protein having essentially the same characteristics as the native protein. Such characteristics can include, for example, immunological reactivity, enzyme activity, structural protein integrity, etc. Structural differences are considered de minimus if there is a significant amount of sequence overlap or similarity between two or more different sequences or if the different sequences exhibit similar physical properties. In the case of a nucleotide sequence, the different sequences will preferably have at least 50 percent, more preferably 70 percent, most preferably 90 percent or more sequence similarity between them. In the case of amino acid sequences, the different sequences have at least 70 percent, more preferably 80 percent, and most preferably 90 percent or more similarity between the polypeptides coded for by the amino acid sequences. Physical properties that may be similar include, for example, electrophoretic mobility, chromatography similarities, sediment gradient coefficients, spectrophotometric properties, etc.

Substrate Utilizing Protein: A protein that provides enzymatic activity, which enzymatic activity includes the ability to directly utilize a substrate as an energy source in a metabolic pathway or which converts a precursor of a substrate to a substrate that can be utilized as an energy source in a metabolic pathway.

Transcription Initiation Site: The nucleotide base in a DNA sequence of a gene at which mRNA transcription begins.

Unassociated Coding DNA Sequence: Part or all of a coding DNA sequence which is not naturally found with the regulatory region of the hybrid gene of which it is a part. As such, an unassociated coding DNA sequence would include a naturally occurring coding DNA sequence with a regulatory region different from the one with which it is naturally associated as well a modified coding DNA sequence (altered from the natural DNA coding sequence by additions, deletions or substitutions of nucleotides in the sequence) with any regulatory region (including a regulatory region that may naturally be found with the coding DNA sequence in its unaltered or natural sequence). Preferably, an unassociated coding DNA sequence will have a regulatory region and a coding DNA sequence, each of which is naturally occurring individually but not naturally occurring together.

The present invention comprises a gene comprising a DNA sequence coding for one or more substrate utilizing protein, wherein said substrate utilizing protein confers a competitive effective ability to utilize a substrate by a microorganism in which it is genetically engineered.

The DNA sequence codes for one or more substrate utilizing protein as previously defined and such a DNA sequence can be referred to as a substrate utilizing DNA sequence. In addition to coding for a substrate utilizing protein in its naturally occurring state, the DNA sequence will confer a competitive effective ability to utilize a substrate by a microorganism into which it is genetically engineered.

The DNA sequences can be obtained from any organism, preferably microorganisms, more preferably prokaryotic microorganisms, most preferably gram negative bacteria.

The method of obtaining the DNA sequences are generally known in the art and they include the transposon mutagenizing method and the random cloning method.

In the transposon mutagenizing method, transposons, e.g., Tn5, are randomly inserted into an organism known to have an ability to utilize a given substrate. Obtention of a mutant that has lost the ability to utilize the substrate means that the insertion of the transposon is in a genetic region critical to the utilization of the substrate. Genetic regions flanking the transposon can then be used to probe the wild-type (non-transposon mutagenized) organism to obtain a genetic fragment conferring the substrate utilization ability. The transposon mutagenizing method is more fully described in Example 3 of the present invention and in copending U.S. patent application Ser. No. 244,813, filed Sep. 14, 1982.

In the random cloning method, a total genomic plasmid library is constructed of an organism having an ability to utilize a given substrate and the plasmids are transferred into a suitable expression host, preferably an organism lacking the ability to utilize a given substrate. Those transformed organisms having an ability to utilize the substrate after transformation are selected, the plasmid removed and the genetic fragment from the total genomic library (conferring the substrate utilization ability) is also removed. The random cloning method is more fully described in Example 5 of the present invention and in copending U.S. patent application Ser. No. 508,375, filed Apr. 11, 1990.

In either the transposon mutagenizing method and the random cloning method, the genetic fragment conferring the substrate utilization ability can be subcloned to find an optimal or minimal sized fragment of DNA conferring the substrate utilization ability [Sambrook et al., *Molecular Cloning: A Laboratory Manual* 2nd Edition, Cold Spring Harbor Laboratory Press, Cold Spring Harbor, N.Y. (1989)].

Types of microorganisms useful in the present invention to genetically engineer with the substrate utilizing DNA sequence are any microorganism, preferably a microorganism that is associated with plants (plant associated microorganism), more preferably a microorganism selected from the group consisting of Pseudomonas, Xanthomonas, Rhizobium, Agrobacterium, Enterobacter and Erwinia, most preferably Pseudomonas.

Genetically engineered microorganisms can be produced using known methods of introducing foreign DNA. Such methods include transformation with chemicals, e.g., Calcium Chloride; transformation using electroporation; bacterial conjugation with bacterial plasmids; transduction using bacterial phages; and transfection using bacterial phage DNA [see, Grinsted et al. editors, *Methods in Microbiology* Volume 21, Academic Press, New York (1988) and Sambrook et al., *Molecular Cloning: A Laboratory Manual* 2nd Edition, Cold Spring Harbor Laboratory Press, Cold Spring Harbor, N.Y. (1989)].

The substrates utilized by the substrate utilizing microorganisms includes any carbon source such as carbohydrates and sugars, amino acids and their derivatives, and fatty acids. Preferably, the substrate is a carbohydrate or sugar, more preferably a sugar or sugar derivative selected from the group consisting of arabinose, xylose, rhamnose, mannopine, octopine, agropine, agrocinopine and hopaline, most preferably mannopine or arabinose. The substrate occurs in the environment of the genetically engineered microorganism in a substantial amount, which is an amount sufficient to be a significant carbon source. Preferably, the substrate will be at least one percent of the total carbon source, preferably at least 5 percent of the total carbon source, most preferably 5 to 10 percent of the total carbon source.

As a result, the genetically engineered microorganisms will have a competitive effective ability to utilize certain substrates in the environment. A competitive effective ability is the preferential ability of a microorganism to utilize a given substrate compared to other microorganisms as defined previously.

In addition to the DNA sequence coding for one or more substrate utilizing protein, the present invention also embodies the microorganisms which have been genetically engineered to contain the DNA conferring a competitive effective ability to utilize a substrate. Preferably, the genetically engineered microorganism contains substrate utilizing DNA sequences that do not naturally occur in the microorganism into which it has been genetically engineered such that the genetically engineered microorganism has a detectable ability to utilize a certain substrate compared to an undetectable ability to utilize the same substrate in the same microorganism that has not been genetically engineered.

The present invention also encompasses a method for enhancing colonization of desired microorganisms in a localized environment comprising introducing into said localized environment a genetically engineered microorganism according to another aspect of the present invention. A localized environment is an environment that is delineated from an external environment by spatial boundaries as defined previously. A preferred localized environment is any localized environment that interfaces with a plant cell. More preferably, the localized environment is the rhizosphere. Preferably, the localized environment contains the substrate to be utilized by the genetically engineered substrate utilizing microorganism in a substantial amount. A substantial amount of the substrate to be utilized by the substrate utilizing microorganism can occur naturally in the localized environment or it can be added to a localized environment lacking a substantial amount of the substrate to bring the amount of the substrate to a substantial level.

Such a substrate can be added as a chemical in a formulation with other fertilizers, pesticides, or any agricultural formulation or composition that is known in the art. Additionally, the substrate can be added as an exudate from plant. Although a plant may produce the substrate as a natural exudate, the plant can also produce the substrate because it has been genetically engineered to do so. Such a genetically engineered plant will produce a substantial amount of the substrate in the localized environment containing the genetically engineered microorganism with a competitive effective ability to utilize the substrate. Although the substrate produced by the genetically engineered plant can be any compound capable of being a carbon source, preferred substrates are the sugars, more preferably the opines or arabinose, more preferably octopine, hopaline, agropine, agrocinopine, mannopine or arabinose, most preferably mannopine or arabinose.

Genes that produce the substrate can be obtained from microorganisms [Tempe and Goldman, "Occurrence and Biosynthesis of Opines", in *Molecular Biology of Plant Tumors*, (Kahl and Schell, eds.), Academic Press, New York pp. 427–449] or plants.

Such a substrate producing DNA can be introduced into a crop species of interest, allowing the crop to be able to produce the desired carbon source that is produced by the protein or proteins coded by the substrate producing DNA.

The coding DNA sequence to be introduced into the plant cell can be introduced into the plant cell in a number of ways that are well known to those of skill in the art. For example, methods of transforming plant cells include microinjection (Crossway et al., *BioTechniques* 4: 320–334 (1986)), electropotation (Riggs et al., *Proc. Nat. Acad. Sci.* USA 83:5602–5606 (1986)), Agrobacterium mediated transformation (Hinchee et al. *Biotechnology* 6: 915–921 (1988)), direct gene transfer (Paszkowski et al., *EMBO J.* 3:2717–2722 (1984)), and ballistic particle acceleration using devices available from Agracetus, Inc., Madison, Wisc. and Dupont, Inc., Wilmington, Del. (see, for example, Sanford et al., U.S. Pat. No. 4,945,050; and McCabe et al., *Biotechnology* 6:923–926 (1988)). Also see, Weissing et al., *Annual Rev. Genet.* 22:421–477 (1988); Sanford et al., *Particulate Science and Technology* 5:27–37 (1987)(onion); Christou et al., *Plant Physiol.* 87: 671–674 (1988) (soybean); McCabe et al., *Bio/Technology* 6:923–926 (1988) (soybean); Datta et al., *Bio/Technology* 8:736–740 (1990)(rice); Klein et al., *Proc. Nat. Acad. Sci. USA* 85:4305–4309 (1988)(maize); Klein et al, *Bio/Technology* 6:559–563 (1988)(maize); Klein et al., *Plant Physiol.* 91:440–444 (1989)(maize); Fromm et al., *Bio/Technology* 8:833–839 (1990); Gordon-Kamm et al., *Plant Cell* 2:603–618 (1990)(maize); and Pace et al., copending U.S. patent application Ser. No. 573,105, filed Aug. 24, 1990, entitled Production of Transgenic Elite Maize Plants and Their Progeny (elite maize).

In addition to the coding sequence of interest, DNA corresponding to suitable regulatory regions can be placed upstream to the coding sequence to enhance transcription of the coding sequence. Alternatively, the coding sequence of interest can be transformed into the plant suitably downstream to a suitable transcriptional regulatory region so as to enhance transcription of the coding region.

Transformation of the plant cells includes separating transformed cells from those that have not been transformed. One convenient method for such separation or selection is to incorporate into the material to be inserted into the transformed cell a gene for a selection marker. As a result, only those cells that have been successfully transformed will contain the marker gene. The translation product of the marker gene will then confer a phenotypic trait that will make selection possible. Usually the phenotypic trait is the ability to survive in the presence of some chemical agent, such as an antibiotic, e.g., kanamycin, G418, paromomycin, etc., which is placed in a selection media.

Once the transformed plant cells have been cultured on the selection media, surviving cells are selected for further study and manipulation. Selection methods and materials are well known to those of skill in the art, allowing one to choose surviving cells with a high degree of predictability that the chosen cells will have been successfully transformed with exogenous DNA.

After transformation of the plant cell or plant, those plant cells or plants transformed by the Ti plasmid so that the enzyme is expressed, can be selected by an appropriate phenotypic marker. These phenotypical markers include, but are not limited to, antibiotic resistance. Other phenotypic markers are known in the art and may be used in this invention.

All plants from which protoplasts can be isolated and cultured to give whole regenerated plants can be transformed by the present invention so that whole plants are recovered which contain the DNA coding sequence. Some suitable plants include, for example, species from the genera Fragaria, Lotus, Medicago, Onobrychis, Trifolium, Trigonella, Vigna, Citrus, Linum, Geranium, Manicot, Daucus, Arabidopsis, Brassica, Raphanus, Sinapis, Atropa, Capsicum, Datura, Hyoscyamus, Lycopersion, Nicotiana, Solanum, Petunia, Dactylis, Majorana, Cichorium, Helianthus, Lactuca, Bromus, Asparagus, Antirrhinum, Hemerocallis, Nemesia, Pelargonium, Panicum, Pennisetum, Ranunculus, Senecio, Salpiglossis, Cucumis, Browallia, Glycine, Lolium, Zea, Triticum, Sorghum and Datura.

There is an increasing body of evidence that practically all plants can be regenerated from cultured cells or tissues, including but not limited to, all major cereal crop species, sugarcane, sugar beet, cotton, fruit and other trees, legumes and vegetables. Limited knowledge presently exists on whether all of these plants can be transformed by Agrobacterium. Species which are a natural plant host for Agrobacterium may be transformable in vitro. Monocotyledonous plants, and in particular, cereals and grasses, are not natural hosts to Agrobacterium. Attempts to transform them using Agrobacterium have been successful recently (Hooykas-Van Slogteren et al., *Nature* 311:763–764 (1984)). There is growing evidence now that certain monocots can be transformed by Agrobacterium. Using current experimental approaches that have now become available, cereal and grass species may be transformable.

Additional plant genera that may be transformed by Agrobacterium include Ipomoea, Passiflora, Cyclamen, Malus, Prunus, Rosa, Rubus, Populus, Santalum, Allium, Lilium, Narcissus, Ananas, Arachis, Phaseolus and Pisum.

Plant regeneration from cultural protoplasts is described in Evans et al., "Protoplast Isolation and Culture," in *Handbook of Plant Cell Culture* 1:124–176 (MacMillan Publishing Co., New York 1983); M. R. Davey, "Recent Developments in the Culture and Regeneration of Plant Protoplasts," *Protoplasts* 1983); P. J. Dale, "Protoplast Culture and Plant Regeneration of Cereals and Other Recalcitrant Crops," in *Protoplasts* 1983—Lecture Proceedings, pp. 31–41 (Birkhauser, Basel, 1983); and H. Binding, "Regeneration of Plants," in *Plant Protoplasts*, pp. 21–37 (CRC Press, Boca Raton, 1985).

Regeneration varies from species to species of plants, but generally a suspension of transformed protoplasts containing multiple copies of the desired gene is first provided. Embryo formation can then be induced from the protoplast suspensions, to the stage of ripening and germination as natural embryos. The culture media will generally contain various amino acids and hormones, such as auxins and cytokinins. It is also advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable.

The mature plants, grown from the transformed plant cells, are selfed to produce an inbred plant. The inbred plant produces seed containing the hybrid gene. These seeds can be grown to produce plants that have the hybrid gene. Such transformed plants and seeds are known as transgenic plants and seeds. Preferred transgenic plants are transgenic crops, which are plants suitable for human cultivation, more preferably plants all or part of which are fit for consumption by animals raised as a source of human food, e.g., livestock, poultry, fish, etc.

The genetically engineered bacteria of the present invention can be used as an active ingredient in a soil compatible formulation or composition. Such bacteria applied in a soil compatible composition, particularly a seed coating, will colonize the plant's emerging roots, thereby affording protection against undesired microorganisms. A preferred soil compatible composition is a seed coating. Examples of soil compatible formulations can be found in European Patent Application 320 483, published Jun. 14, 1989; U.S. Pat. Nos. 4,875,921 and 4,877,738.

The active ingredients of the present invention are normally applied in the form of compositions and can be applied to the crop area or plant to be treated, simultaneously or in succession, with further compounds. These compounds can be both fertilizers or micronutrient donors or other preparations that influence plant growth. They can also be selective herbicides, insecticides, fungicides, bactericides, nematicides, mollusicides or mixtures of several of these preparations, if desired, together with further carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers.

Preferably, the active ingredients may be applied to seeds (coating) by impregnating the seeds either with a liquid formulation containing active ingredients, or coating them with a solid formulation. The active ingredients can also penetrate the plant through the roots via the soil (systemic action) by impregnating the locus of the plant with a liquid composition, or by applying the compounds in solid form to the soil, e.g. in granular form (soil application). Another method of applying active ingredients of the present invention or an agrochemical composition which contains at least one of the active ingredients is leaf application. The number of applications and the rate of application depend on the intensity of infestation by the corresponding pathogen (type of fungus). In special cases, further types of application are also possible, for example, selective treatment of the plant stems or buds.

The active ingredients are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations, for example, in polymer substances. Like the nature of the compositions, the methods of application, such as spraying, atomizing, dusting, scattering or pouring, are chosen in accordance with the intended objectives and the prevailing circumstances. Advantageous rates of application are normally from 50 g to 5 kg of active ingredient (a.i.) per hectare ("ha", approximately 2.471 acres), preferably from 100 g to 2 kg a.i./ha, most preferably from 200 g to 500 g a.i./ha.

The formulations, compositions or preparations containing the active ingredients and, where appropriate, a solid or liquid adjuvant, are prepared in known manner, for example by homogeneously mixing and/or grinding the active ingredients with extenders, for example solvents, solid carriers and, where appropriate, surface-active compounds (surfactants).

Suitable solvents include aqueous buffers, nutrient media, or water.

The solid carriers used e.g. for dusts and dispersible powders, are normally natural mineral fillers such as calcite, talcum, kaolin, montmorillonite or attapulgite, but can also include peat, methylcellulose, vermiculite or potting mixes. In order to improve the physical properties it is also possible to add highly dispersed silicic acid or highly dispersed absorptive polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverized plant residues.

Depending on the nature of the active ingredient to be used in the formulation, suitable surface-active compounds used are nonionic, cationic and/or anionic surfactants having good emulsifying, dispersing and wetting properties. The term "surfactants" will also be understood as comprising mixtures of surfactants.

Anionic surfactants that can be used include fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammoniums salts and have a 8 to 22 carbon alkyl radical which also includes the alkyl moiety of alkyl radicals, for example, the sodium or calcium salt of lignonsulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnapthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants re nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

The surfactants customarily employed in the art of formulation are described, for example, in "McCutcheon's Detergents and Emulsifiers Annual," MC Publishing Corp. Ringwood, N.J., 1979, and Sisely and Wood, "Encyclopedia of Surface Active Agents," Chemical Publishing Co., Inc. New York, 1980.

Sterilized seeds to be protected are coated with the candidate strains at a concentration of $10^6$–$10^8$ bacteria seed. This may be conveniently done by several ways. First, the bacteria are suspended in water containing 0.1M $MgSO_4$ adjusting the population to $10^8$–$10^9$ colony forming units (CFU), and soaking the seeds in the suspension for 30 minutes. Second, the bacteria are added to a suspension containing 0.5 to 2 percent of a suspending agent such as methylcellulose in water (eight plates of bacteria per 50 ml methylcellulose solution per 100 g seed) and the seeds are dried overnight.

The agrobacterial compositions usually contain from about 0.1 to about 99%, preferably about 0.1 to about 95%, and most preferably from about 3 to about 90% of the active ingredient, from about 1 to about 99.9%, preferably from about 1 to about 99%, and most preferably from about 5 to about 95% of a solid or liquid adjuvant, and from about 0 to about 25%, preferably about 0.1 to about 25%, and most preferably from about 0.1 to about 20% of a surfactant.

Whereas commercial products are preferably formulated as concentrates, the end user will normally employ dilute formulations.

Another method of the present invention is a method of controlling the presence of an undesired microorganism in a localized environment comprising enhancing colonization of a desired microorganism in the same localized environment according to the previous aspect of the present invention.

This method is essentially the same as the method for enhancing colonization of a desired species except that the desired microorganism, possessing a substrate utilizing ability, is present in an antimicrobial effective amount rather than just possessing a competitive effective ability. Thus the population of the substrate utilizing microorganism not only increases more than the population of the non-substrate utilizing microorganism, there is a net decrease in the number of members of the population of the non-substrate utilizing species. As such, the amount of active ingredient, in the form of genetically engineered microorganisms having a superior ability to utilize a certain substrate, can be adjusted to obtain the desired effect of controlling an undesired microorganism in a localized environment. Methods of applying the active ingredient that can be used are the same as for other aspects of the present invention.

EXAMPLES

The following examples are intended to provide guidance to specific embodiments of the present invention without limiting its scope in any way.

Example 1: Identification of Homozygous Mannopine-producing Tobacco Plants

Axenically grown *Nicotiana tabacum* cv. Petit Hayanna SR1 plants are decapitated and suspensions of Agrobacterium Rhizogenes strain 8196 (as described in Chilton et. al., *Nature*, 295:432–434 (1982) and references cited therein) are applied to the wound sites. Transformants are obtained by regenerating plants from roots that formed at the wound sites. Strain 8196 introduces T-DNA into its host plant cells which results in production of mannopine by the transformed plant.

The regenerated plants are tested for mannopine production. One leaf is removed from each plant. To each leaf is added a volume of 70% ethanol equal to the weight of the leaf. The leaf is shred and ground in a mortar with a pestle. The homogenate is cleared by centrifugation for one and a half minute in a microfuge. The supernatant is analyzed for the presence of mannopine as described in Chilton, W. S. and Chilton, M.-D., *J. Bacteriol.* 158:650–658 (1984).

Mannopine-producing (MOP$^+$) regenerants are allowed to self-fertilize and set seed. Plants grown from such seeds are again tested for mannopine production, allowed to self-fertilize and set seed, and the process is repeated for three generations to obtain homozygous mannopine-producing plants.

Mannopine is recoverable from the medium in which these plants had been grown. Seeds are surface sterilized by soaking in 20% chlorox for 6 minutes. They are then rinsed extensively with sterile water and allowed to germinate and grow in water agar plates. After 3 weeks, the plantlets are gently removed from the agar. The agar is dialyzed against 25 volume of water:methanol (9:1). Opine content in the water:methanol fraction is determined as described in Chilton, W. S. and Chilton, M.-D., *J. Bacteriol.* 158:650–658 (1984).

Example 2: Identification of Mannopine-utilizing Pseudomonas

A Pseudomonas strain capable of using mannopine as the sole carbon source is isolated from a soil sample from the cellar of a pear nursery. To 1 g. of freshly collected soil is added 1 ml of selective medium containing AT salts, 1 g/l ammonium sulfate, 0.1 mg/l botin, 100 mg/l cycloheximide, and 800 mg/l mannopine. The mixture is incubated at room temperature, in the dark and with shaking. After one week 5 ml of saline is added and the resulting suspension is vortexed to prepare the pre-enriched soil inoculum. 0.1 ml of inoculum is transferred to 1 ml of fresh selective medium, the culture is incubated at 27C with shaking. After evidence of bacterial growth is observed, the culture is diluted 100-fold in 0.85% saline, and 0.1 ml of the dilute suspension is used to inoculate 1 ml of fresh selective medium. Following growth, a loopful of this second culture is transferred to Nutrient Agar (Difco) containing 200 mg/l of cycloheximide. Colonies obtained are further purified on Nutrient Agar and stored in 15% (v/v) glycerol at −70C. The mannopine-utilizing Pseudomonas isolate CGP 11 (deposited with the American Type Culture Collection, Rockville, Md., USA, as ATCC No. 55097, deposited Sep. 27, 1990) is found by the American Type Culture Collection (ATCC) to have the traits typical of the species *Pseudomonas putida*.

Example 3: Isolation of Pseudomonas Mutant Unable to Utilize Mannopine

Strain CGP 11 (deposited with the American Type Culture Collection, Rockville, Md. USA as ATCC 55097, on Sep. 27, 1990) is mutagenized using transposon Tn5 carried on the suicide plasmid pGS9 [in E. coli WA803, Selvaraj, G. and Iyer, V. N., *J. Bacteriol.* 156:1292–1300 (1983) ]. The pGS9 plasmid possesses broad host range N-type transfer genes in a narrow host range p15A replicon. One mutant is identified from 10 different matings (a total of 10,000) clones containing Tn5) .

Example 4: Competition Assay (Comparing Mut$^+$ Wild-type and Mut$^-$ mutant)

Seeds are surfaced sterilized as described in example 1 above. Fresh overnight cultures of bacterial strains CGP 11 (mut$^+$) and its Tn5 mutagenized derivative (Mut$^-$) are adjusted and mixed to produce a bacterial suspension containing approximately $10^6$ cfu (colony forming units)/ml of each strain. The sterilized seeds are soaked in the bacterial suspension for 20 minutes. Representative seeds are placed in sterile water and vortexed vigorously to dislodge the bacteria. The ratio of Mut$^+$/Mut$^-$ bacteria (input ratio) removed from the seeds is determined by plating on L agar and on L agar with kanamycin (50 ug/ml, strain Mut− is kanamycin resistant). The remaining seeds are planted in potting mix previously autoclaved in 50 ml polypropylene disposable centrifuge tubes (Corning). 20 ml of water is added to each tube before autoclaving. The tubes are placed in racks and each rack is covered with plastic wrap. The racks are placed in a growth chamber (Conviron) with day time conditions (14 hours) of 24C and 60% humidity, and night time conditions (10 hours) of 18C and 90% humidity. After 4 weeks, the plants are removed gently from the tubes, and bacteria recovered from the roots by vigorous vortexing. The ratio of Mut+/Mut− bacteria (output ratio) is again determined by plating. The results (see FIG. 1) indicated that in an environment without mannopine (MOP− plants), the Mut+ and Mut− bacteria are equally competitive. There is no change in their ratio from the beginning to the end of the experiment. In the presence of mannopine (MOP+ plants), the Mut+ bacteria increased in abundance relative to the Mut− bacteria, demonstrating that the ability to utilize mannopine is a competitive advantage in such an environment, i.e., the Mut+ strain will increase in numbers relative to the Mut− strain.

Example 5: Construction of Genomic Library and Isolation of Cosmid Clone Containing Mannopine-utilization (Mut) Genes Total genomic DNA is isolated from strain CGP 11 using standard procedures. The DNA is partially digested with Sau3AI to generate fragments in the size range of 20–35 kb. These fragments are cloned into the broad host range cosmid vector pLAFR3, using the strategy of Staskawicz et al., *J. Bacteriol.* 169:5789–5794 (1987), with the modification that the fragments are not dephosphorylated. The cosmid library is mobilized from E. coli strain DH5-alpha to the naturally Mut− *Pseudomonas fluorescens* strain P1855.344 [Dessaux et. al., *Mol. Gen. Genet.* 208:301–308 (1987)], by triparental mating using the helper plasmid pRK2013 as described in Ditta et. al., *Proc. Natl. Acad. Sci.* USA 77:7347–7351 (1980). Mut+ recombinants are identified and a cosmid clone, pCIB117 (deposited with the American Type Culture Collection, Rockville, Md. USA as ATCC Accession Number 68429 on Sep. 27, 1990), is isolated which is shown to confer Mut+ phenotype to naturally Mut− Pseudomonas.

Example 6: Transfer of Mut Genes and pLAFR into Recipient Pseudomonas Strains

A number of methods can be used to transfer the Mut genes into recipient Pseudomonas strains, including the ones described in this example. The transferred DNA can be maintained on a plasmid or integrated into the recipient chromosome. The latter is preferred for long-term stable maintenance of the transferred genes in the recipient.

The cosmid clone pCIB117, which contains the Mut genes, has a broad host range. It can be introduced into, and stably maintained in, a large number of gram-negative bacteria, including Pseudomonas. A preferred method of introducing into Pseudomonas is by triparental mating as described in Ditta et. al., *Proc. Natl. Acad. Sci.* USA 77:7347–7351 (1980).

A more refined approach would first determine the limits of the Mut genes. This can be achieved by constructing subclones of pCIB117 containing different amounts of genetic material and testing each for its ability to confer Mut+ phenotype. Alternatively, the limits of the Mut genes can be determined by localized transposon mutagenesis, mapping of the transposon insertions, and testing the Mut phenotype of the insertion mutants, as described in de Bruijn and Lupski, *Gene* 27:131–149 (1984). The smallest Mut+ gene fragment can then be introduced into the recipient chromosome.

A site in the chromosome of the recipient would have to be chosen, where an insertion would not cause deficiencies in competitiveness of the organism in the environment in which it is to be applied. Such sites can be identified by transposon mutagenesis (using a transposon with a selectable marker such as drug resistance) followed by analysis of the competitiveness of the insertion mutants as described in copending U.S. patent application Ser. No. 244,813, filed Sep. 14, 1988. The transposon insertion site and flanking sequences can be cloned by selecting for the drug resistance encoded by the transposon. The flanking sequences can then be used as a hybridization probe to identify and isolate the wild type genetic segment containing the insertion site from a genomic clone bank of the recipient chromosome, using standard cloning techniques. The Mut gene fragment can be inserted into an appropriate site in the recipient gene segment and the resulting recombinant sequence integrated into the recipient chromosome by gene replacement [Ruvkun, G. B., Sundaresan, V., and Ausubel, F. M., *Cell* 29:551–559 (1982)]. Alternatively, the transposon sequence itself can provide the homology for integration of the Mut genes into a recipient containing an inserted transposon.

These Pseudomonas recipient strains that have received a recombinant Mut gene can be compared to wild type recipient strains using a competition assay as described in Example 4. The Mut containing strains have a competitive advantage in an environment containing mannopine, i.e., they will increase in numbers relative to the wild type strains.

Example 7: Survey of Sugar Utilization by Pseudomonas

Pseudomonas strains are tested for their ability to grow on minimal media containing individual sugars as sole carbon sources (Table 1). The basic minimal medium contained: 0.4% $KH_2PO_4$, 0.4% $Na_2HPO_4$, 0.02% $MgSO_4$, 0.0005% $FeCl_2$, and 0.1% $NH_4SO_4$. Solid medium also contained 1.5% agar. Little or no bacterial growth could be observed on this medium without added sugar. The sugars to be tested are added to a final concentration of 0.2%. Six sugars known to be present in wheat root exudate are tested: glucose, fructose, arabinose, xylose, rhamnose, and maltose. Observations are made 24 hours, 48 hours, and 7 days after bacterial cells are transferred on to the various minimal-sugar plates. It is generally believed that fluorescent pseudomonads are extremely versatile in utilizing nutrients in root exudates. Our results showed that xylose, arabinose, and rhamnose, three abundant sugars in wheat root exudate, are utilized by only a fraction of the strains tested.

TABLE 1

GROWTH OF STRAINS ON MINIMAL MEDIA CONTAINING INDIVIDUAL SUGARS

| Strain # | glucose | fructose | arabinose | xylose | maltose | rhamnose |
|---|---|---|---|---|---|---|
| 897 | + | + | + | + | | |
| 898 | + | + | + | + | | w |
| 899 | + | + | + | + | | |
| 900 | + | + | + | + | | w |
| 913 | + | + | + | + | | |
| 914 | + | + | | | | |
| 915 | + | + | + | | | w |
| 916 | + | + | | | | |
| 917 | + | + | + | + | | |
| 918 | + | + | | | | |
| 919 | | n | | + | | |

TABLE 1-continued

GROWTH OF STRAINS ON MINIMAL MEDIA
CONTAINING INDIVIDUAL SUGARS

| Strain # | glu-cose | fructose | arabinose | xylose | maltose | rhamnose |
|---|---|---|---|---|---|---|
| 920 | + | + |   |   |   | w |
| 921 | + | + |   |   |   |   |
| 922 | + | + |   |   |   |   |
| 923 | + | + |   |   |   |   |
| 924 | + | + | + | + |   | w |
| 927 | + | + | + | + | + | + |
| 928 |   | w |   | + | + | w |
| 929 | + | + | + | + |   |   |
| 930 | + | + | + | + |   |   |
| 931 | + | + | + | + |   |   |
| 932 | + | n | + |   |   |   |
| 933 | + | + | + | + |   | w |
| 934 | + | + |   |   |   |   |
| 935 | + | + |   |   |   |   |
| 936 |   |   |   | + |   |   |
| Pf5 | + | + |   |   |   |   |

+ = growth,
w = weak growth,
n = not tested

Example 8: Competition Assay (Comparing Ara⁺ Wild-type and Ara⁻ Mutant)

The isolation of the Ara– mutant 98D12 from strain 2-79 (NRRL-B15132) has been described in copending U.S. patent application Ser. No. 576,259, filed Aug. 31, 1990. The relative competitiveness of the two strains are compared in an assay identical to the one described in example 4, with the exception that the host plant is wheat, and the length of the assay is seven days. The results (Table 2) indicate that the $Ara^+$ strain had a competitive advantage over its isogenic, $Ara^-$ mutant.

TABLE 2

Competitiveness of an Arabinaose Non-utilizing Mutant vs. the Wild-type

|  | $Ara^+$ Bacteria (%) | $Ara^-$ Bacteria (%) |
|---|---|---|
| Input | 33 | 67 |
| Output | 66 | 34 |

We claim:
1. An isolated and purified DNA sequence, obtainable from a Pseudomonad, which consists of at least one gene capable of conferring a mannopine utilizing phenotype upon a genetically engineered microorganism, wherein said DNA sequence is contained in pCIB117.
2. A plasmid containing the DNA sequence of claim 1.
3. An isolated *Pseudomonas putida* strain having all the identifying characteristics of *Pseudomonas putida* ATCC 55097.
4. A genetically engineered Pseudomonas bacterium having stably and functionally incorporated therein the DNA sequence of claim 1.
5. A bacterium of claim 4, which is *Pseudomonas putida* or *Pseudomonas fluorescens*.
6. A method of enhancing colonization of a desired bacterium in a localized environment of a plant, comprising genetically transforming said desired bacterium with the DNA sequence of claim 1, and introducing said bacterium into the environment.
7. A method of enhancing colonization of a desired bacterium in a localized environment of a plant, comprising genetically transforming said desired bacterium with the plasmic of claim 2 and introducing said bacterium into the environment.

* * * * *